United States Patent
McGuckin, Jr.

(10) Patent No.: US 7,922,757 B2
(45) Date of Patent: Apr. 12, 2011

(54) VASCULAR CONDUIT

(75) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 635 days.

(21) Appl. No.: 11/974,242

(22) Filed: Oct. 12, 2007

(65) Prior Publication Data
US 2008/0132924 A1    Jun. 5, 2008

Related U.S. Application Data

(60) Provisional application No. 60/853,843, filed on Oct. 23, 2006.

(51) Int. Cl.
*A61F 2/06* (2006.01)

(52) U.S. Cl. ....................................... 623/1.23; 606/153

(58) Field of Classification Search .................. 606/153, 606/155, 158; 604/264, 506, 510, 523, 8; 623/1.11, 1.13, 1.23
See application file for complete search history.

(56) References Cited

U.S. PATENT DOCUMENTS

| | | | |
|---|---|---|---|
| 3,788,328 A * | 1/1974 | Alley et al. | 604/178 |
| 4,493,696 A | 1/1985 | Uldall | |
| 4,666,426 A | 5/1987 | Aigner | |
| 5,057,073 A | 10/1991 | Martin | |
| 5,167,623 A | 12/1992 | Cianci et al. | |
| 5,195,962 A | 3/1993 | Martin et al. | |
| 5,480,380 A | 1/1996 | Martin | |
| 5,931,829 A | 8/1999 | Burbank et al. | |
| 5,989,206 A | 11/1999 | Prosl et al. | |
| 5,989,213 A | 11/1999 | Maginot | |
| 6,123,725 A | 9/2000 | Aboul-Hosn | |
| 6,146,373 A | 11/2000 | Cragg et al. | |
| 6,156,016 A | 12/2000 | Maginot | |
| 6,190,371 B1 | 2/2001 | Maginot et al. | |
| 6,454,997 B1 | 9/2002 | Divino, Jr. et al. | |
| 6,475,207 B1 | 11/2002 | Maginot et al. | |
| 6,582,409 B1 | 6/2003 | Squitieri | |
| 6,585,705 B1 | 7/2003 | Maginot et al. | |
| 6,620,118 B1 | 9/2003 | Prosl et al. | |
| 6,645,194 B2 | 11/2003 | Briscoe et al. | |
| 6,692,473 B2 | 2/2004 | St. Cyr et al. | |
| 6,723,084 B1 | 4/2004 | Maginot et al. | |
| 6,743,218 B2 | 6/2004 | Maginot et al. | |
| 6,758,836 B2 | 7/2004 | Zawacki | |
| 6,808,510 B1 | 10/2004 | DiFiore | |
| 6,969,379 B1 | 11/2005 | Aboul-Hosn et al. | |
| 7,060,060 B1 | 6/2006 | Simpson et al. | |
| 2002/0107506 A1 | 8/2002 | McGuckin, Jr. et al. | |
| 2002/0121282 A1 | 9/2002 | McGuckin, Jr. et al. | |
| 2003/0093027 A1 * | 5/2003 | McGuckin et al. | 604/6.16 |
| 2006/0064159 A1 * | 3/2006 | Porter et al. | 623/1.24 |

FOREIGN PATENT DOCUMENTS

WO    2006026687    3/2006

* cited by examiner

*Primary Examiner* — Michael J Milano
*Assistant Examiner* — Victor X Nguyen
(74) *Attorney, Agent, or Firm* — Neil D. Gershon

(57) ABSTRACT

A vascular system including a catheter having a first end portion, a second end portion and a plurality of lumens wherein the first end portion is dimensioned for insertion into a vascular graft and the second end portion is dimensioned for insertion into a vein of a patient to create a conduit from an artery to the vein.

10 Claims, 2 Drawing Sheets

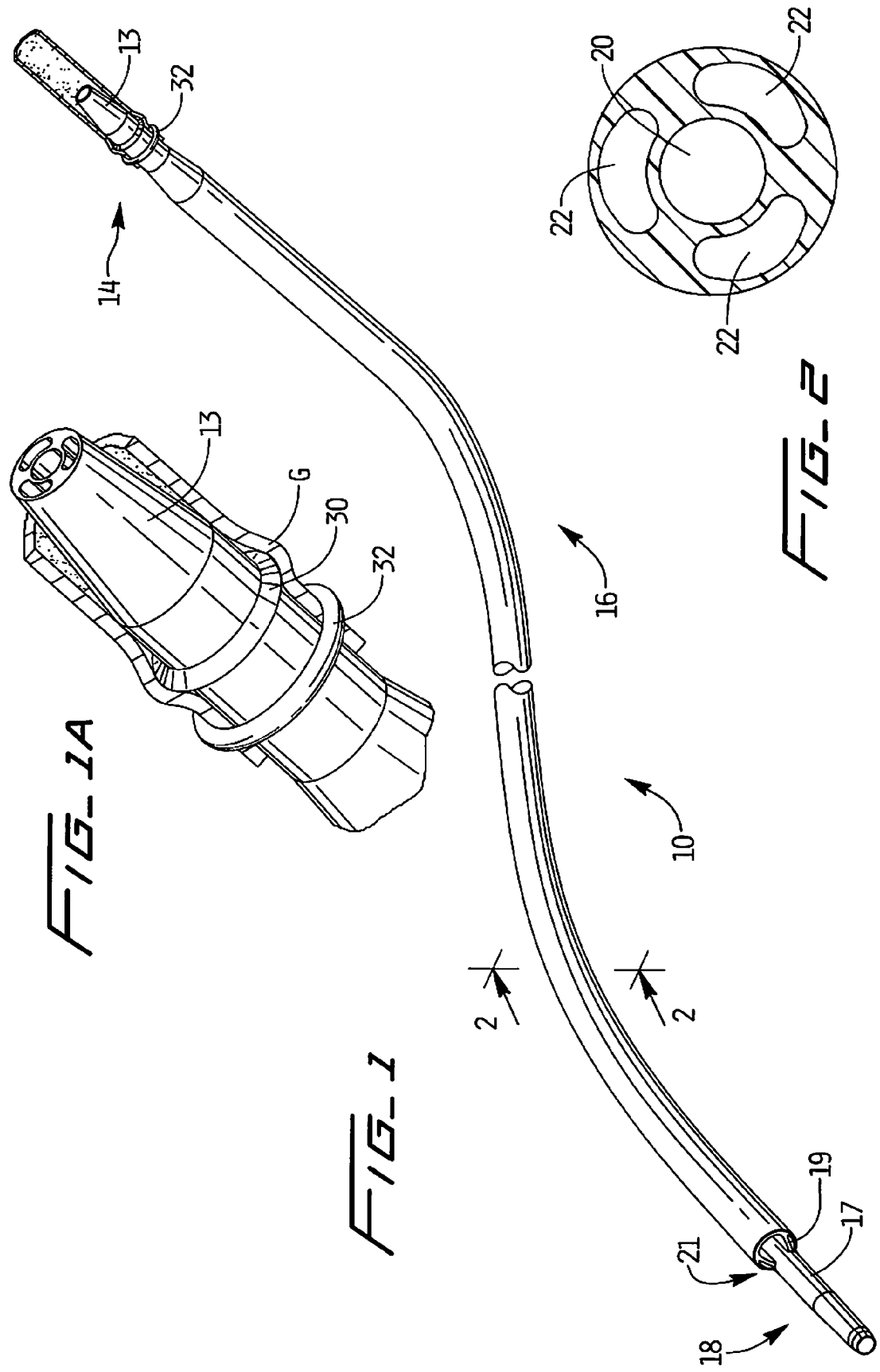

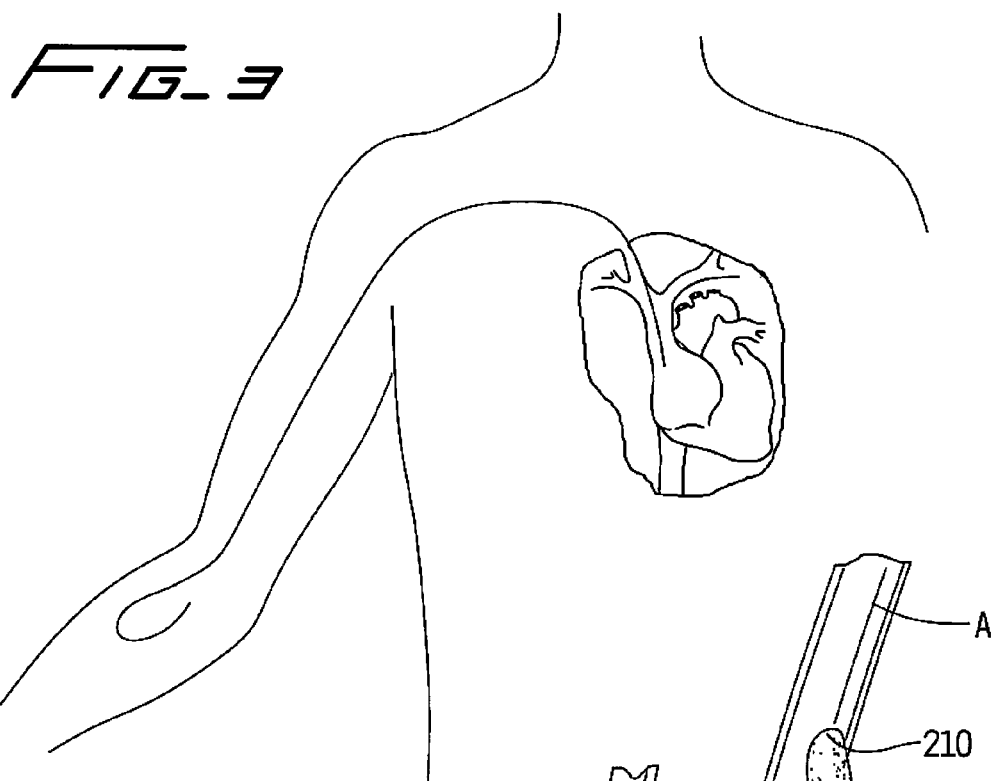
FIG_3
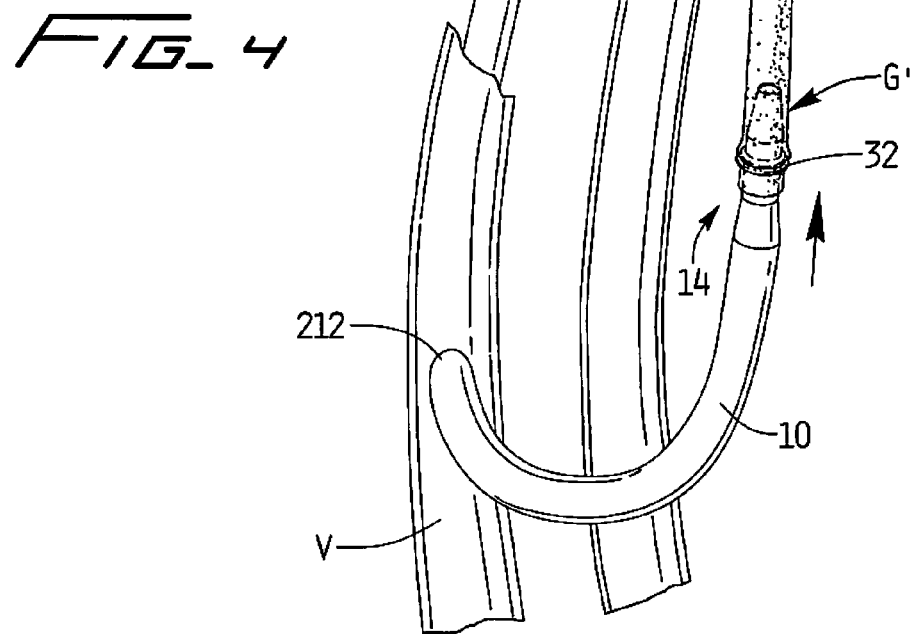
FIG_4

VASCULAR CONDUIT

This application claims priority from provisional application Ser. No. 60/853,843, filed on Oct. 23, 2006. The entire contents of the application is incorporated herein by reference.

BACKGROUND

1. Technical Field

This application relates to a vascular device and more particularly to a vascular conduit for fluidly connecting a graft to a vein.

2. Background of Related Art

Hemodialysis is a well-known method of simulating renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients suffering from chronic renal insufficiency, hemodialysis is life saving because it provides a machine to simulate the function of the kidneys, thereby enabling the patients to live independently between dialysis treatments.

In the hemodialysis procedure, blood is withdrawn from the patient's body and transported to a dialysis machine, also commonly referred to as a kidney machine. In the dialysis machine, toxins and other waste products diffuse through a semi-permeable membrane into a dialysis fluid closely matching the chemical composition of the blood. The filtered blood, i.e. with the waste products removed, is then returned to the patient's body.

In one approach, an arteriovenous fistula is created so a high rate of blood flows from the artery into the patient's vein. The blood is then withdrawn directly from the patient's vein (native vein fistula) providing high rates of blood flow. Since this approach requires multiple needle sticks in the vein to withdraw and return the blood, the vein can eventually be damaged beyond usability, blood clots can form and the vein can fail. Once the vein fails, it could no longer be used for access and an alternate site must be utilized.

To avoid the repetitive damage to the vein, dialysis grafts are used. These grafts, typically made of PTFE, are implanted under the patient's skin, typically in the patient's forearm, and the graft is sutured at one end to the vein (venous anastomosis) for outflow and at the other end to the artery (arterial anastomosis) for inflow. The graft is also typically a loop graft to provide greater access area. This graft, which functions as a shunt creating high blood flow from the artery to the vein, enables access to the patient's blood without having to directly puncture the vein. That is, the technician sticks the two needles into the graft to respectively withdraw and return blood to the patient, with the inlet on the arterial side for blood requiring filtration processing and the outlet on the vein side for return of processed blood from the dialysis machine.

The dialysis graft, especially on the venous side, may become inoperable after a period of time due to thrombus or clots formed at the anastomosis site.

U.S. Pat. No. 6,582,409 describes a vascular access system comprising a PTFE tube and a silastic catheter. The tube is used to create an arteriovenous fistula with one end sewn to an artery and the silastic catheter end placed into the venous system. This system includes needle access sites.

The need exists for a system which can be used with existing grafts to avoid the disadvantages associated with a graft venous anastomosis site.

SUMMARY

The present invention advantageously provides a vascular system comprising a catheter having a first end portion, a second end portion and a plurality of lumens, wherein the first end portion is dimensioned for insertion into a vascular graft and the second end portion is dimensioned for insertion into a vein of a patient to create a conduit from the artery to the vein.

The system preferably further includes a connector connecting the catheter to the graft. The connector is preferably disposed over an increased diameter area of the catheter. In one embodiment, the connector comprises a locking ring placed on an exterior surface of the catheter. The connector can comprise a slidable locking member movable between a first position and a second position to compress the graft against an exterior surface of the catheter. Preferably, in the second position the locking member clamps the graft against a raised surface of the catheter.

Preferably, the first end of the catheter is tapered and the second end has a reduced diameter portion. The catheter preferably comprises a plurality of lumens, wherein in a preferred embodiment the plurality of lumens comprises a circular central lumen and at least two lumens radially spaced from the central lumen.

The present invention also provides a method for providing a vascular conduit from a patient's artery to vein comprising the steps of:

providing a catheter having at least two lumens;

inserting a first portion of the catheter into a graft connected to an artery of the patient;

connecting a first region of the catheter to the graft;

inserting a second portion of the catheter through a vein of the patient and through the vascular system.

The step of connecting the first region can comprise the step of sliding a locking member over a raised surface of the catheter.

BRIEF DESCRIPTION OF THE DRAWINGS

Preferred embodiment(s) of the present disclosure are described herein with reference to the drawings wherein:

FIG. 1 is an isometric view of the catheter conduit of the present invention;

FIG. 1A is a close up view of the tip of the catheter inserted in the graft and the locking ring shown in the proximal position before clamping the graft onto the catheter conduit;

FIG. 2 is a cross-sectional view taken along line 2-2 of FIG. 1;

FIG. 3 is a schematic of the catheter conduit shown extending from the patient's arm thought the vascular system; and FIG. 4 illustrates the catheter conduit fluidly connecting a vascular graft to a vein.

DETAILED DESCRIPTION OF PREFERRED EMBODIMENTS

Referring now in detail to the drawings where like reference numerals identify similar or like components throughout the several views, FIG. 1 illustrates the apparatus of the present invention, designated generally by reference numeral 10, which functions as a vascular conduit.

Apparatus 10 has a first end portion 14, a second end portion 18 and an intermediate portion 16. The apparatus is in the form of a catheter and functions as a conduit and has a lumen configuration best seen in FIG. 2 comprising a central lumen 20 dimensioned to slide over a guidewire and three radially somewhat kidney-shaped lumens 22 spaced substantially equidistantly from the central lumen 20. This lumen configuration is shown and described in commonly assigned U.S. Pat. No. 7,077,829, the entire contents of which are incorporated herein by reference.

The first end portion 14 of catheter 10 includes a tapered region 13 to facilitate entry into the graft. A raised surface area 30 and sliding ring 32 are shown on the exterior surface of the catheter 10, the function of which is described in detail below. The raised surface 30 increases the diameter of the catheter 10 at that area. The raised surfaced is shown as a ring but can include other surfaces and shapes. The raised surface can be integral with the catheter or a separate component attached to the catheter.

Second end portion 18 has a reduced diameter portion 17 starting at transition region 21 formed by extension walls 19 in the same manner as in the U.S. Pat. No. 7,077,829.

In use, the first end portion 14 is inserted into graft G which is attached at a first region to the vessel, i.e. artery, A as shown in FIG. 4. To retain the distal portion inside the graft, ring 32 is slid along the catheter body and over the graft G in a direction of the arrow to a position over the surface 30. As it is forced over the surface 30 (shown in the form of a connecting ring), it clamps the graft between the ring 32 and surface 30 as it presses the graft G against the surface 30 of the catheter 10. FIGS. 1 and 1A illustrate the sliding ring proximal of the connecting ring or surface 30, before securement of the graft G. The sliding ring 32 is shown positioned over the connecting ring 30 in FIG. 4 to connect the catheter to the graft G. The distal end portion 18 of catheter 10 extends within the vein V and up through the venous system.

Consequently, the vascular graft G with the catheter 10 functions as a shunt between the artery A and vein V. Graft G is sutured to the artery at arterial anastomosis site 210 and catheter conduit 10 is inserted into graft G at region G1 and into the vein at site 212 to extend through the vascular system.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A vascular system comprising a catheter having a first end portion, a second end portion at the opposite end of the catheter and a plurality of independent lumens, the first end portion dimensioned for insertion into a vascular graft such that the plurality of lumens are in fluid communication with the vascular graft and the second end portion dimensioned for insertion into a vein of a patient such that the plurality of lumens are open to and in communication with the vein to create a conduit from an artery to the vein further comprising a connector, the connector connecting the catheter to the graft; wherein the connector comprises a slidable locking member movable between a first position and a second position to compress the graft against an exterior surface of the catheter; wherein the exterior surface of the catheter has a raised surface and in the second position, the locking member clamps the graft against a raised surface of the catheter so the graft is positioned between the locking member and the raised surface.

2. The system of claim 1, wherein the connector comprises a locking ring disposed on an exterior surface of the catheter.

3. The system of claim 1, wherein the catheter includes an area of increased diameter, the connector placed over the increased diameter area.

4. The system of claim 3, wherein the increased diameter is in the form of a ring.

5. The system of claim 1, wherein the first end of the catheter is tapered.

6. The system of claim 1, wherein the second end of the catheter has a reduced diameter portion.

7. The system of claim 5, wherein the plurality of lumens comprises a circular central lumen and at least two lumens radially spaced from the central lumen.

8. The system of claim 7, wherein the catheter comprises three radially spaced lumens.

9. The system of claim 8, wherein the radially spaced lumens are substantially kidney shaped in configuration.

10. A method for providing a vascular conduit from a patient's artery to vein comprising:
   providing a catheter having at least two lumens and a raised surface;
   inserting a first region of the catheter into a graft connected to an artery of the patient;
   connecting a first region of the catheter to the graft by sliding a locking ring over the raised surface of the catheter to clamp the graft between the locking ring and raised surface; and
   inserting a second region of the catheter through a vein of the patient and through a vascular system.

* * * * *